United States Patent
Gorbunova et al.

(10) Patent No.: US 9,315,588 B2
(45) Date of Patent: Apr. 19, 2016

(54) COMPOSITIONS AND METHODS FOR RECOMBINANT SYNTHESIS OF HIGH MOLECULAR WEIGHT HYALURONIC ACID

(71) Applicants: Vera Gorbunova, Honeoye Falls, NY (US); Andrei Seluanov, Honeoye Falls, NY (US)

(72) Inventors: Vera Gorbunova, Honeoye Falls, NY (US); Andrei Seluanov, Honeoye Falls, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/376,239

(22) PCT Filed: Feb. 4, 2013

(86) PCT No.: PCT/US2013/024584
§ 371 (c)(1),
(2) Date: Aug. 1, 2014

(87) PCT Pub. No.: WO2013/116819
PCT Pub. Date: Aug. 8, 2013

(65) Prior Publication Data
US 2014/0378678 A1    Dec. 25, 2014

Related U.S. Application Data

(60) Provisional application No. 61/594,929, filed on Feb. 3, 2012.

(51) Int. Cl.
| | |
|---|---|
| *C12P 19/04* | (2006.01) |
| *C08B 37/08* | (2006.01) |
| *C12N 9/10* | (2006.01) |
| *C12P 19/26* | (2006.01) |

(52) U.S. Cl.
CPC .......... *C08B 37/0072* (2013.01); *C12N 9/1051* (2013.01); *C12P 19/04* (2013.01); *C12P 19/26* (2013.01); *C12Y 204/01212* (2013.01); *Y02P 20/52* (2015.11)

(58) Field of Classification Search
None
See application file for complete search history.

(56) References Cited

U.S. PATENT DOCUMENTS

| 6,489,467 B1 | 12/2002 | Carlino et al. |
| 6,660,853 B2 | 12/2003 | Prescott |
| 6,838,086 B1 | 1/2005 | Simon et al. |
| 2010/0136630 A1 | 6/2010 | Stocks et al. |
| 2011/0281817 A1 | 11/2011 | Nielsen et al. |
| 2013/0131009 A1 | 5/2013 | Gorbunova et al. |

FOREIGN PATENT DOCUMENTS

| WO | 94/00463 | 1/1994 |
| WO | 2011/119805 | 9/2011 |

OTHER PUBLICATIONS

Genbank Accession No. EHB01992.1 (Oct. 14, 2011).*
Watanabe et al., The Journal of Biological Chemistry, 1996, vol. 271, pp. 22945-22948.*
Seluanov et al., 2010, "Anticancer mechanisms in a longest-lived rodent, the naked mole-rat.", International Workshop (From *Homo sapiens* to *Homo sapiens* liberates), May 25-26, 2010, p. 13.
Seluanov et al., 2009, "Hypersensitivity to contact inhibition provides a clue to cancer resistance of naked mole-rat." Proc Natl Acad Sci USA, 106(46): 19352-19357.
Salmon et al., 2008. "Fibroblasts from naked mole-rats are resistant to multiple forms of cell injury, but sensitive to peroxide UV light, and ER stress." J Gerontol A Biol Sci Med Sci, 63(3): 232-241.
Sedivy et al., 2009, "How to learn new and interesting things from model systems based on 'exotic' biological species." Proc Natl Acad Sci USA, 106(46): 19207-19208.
Tomida et al., 1977, "Effects of adenosine 3':5'-cyclic monophosphate and serum on synthesis of hyaluronic acid in confluent rat fibroblasts." Biochem J, 162: 539-543.
Seluanov et al., 2008, "Distinct tumor suppressor mechanisms evolve in *rodent* species that differ in size and lifespan." Aging Cell, 7: 813-823.
Yoneda et al., 1988, "Hyaluronic acid modulates proliferation of mouse dermal fibroblasts in culture." Journal of Cell Science, 90: 265-273.
Jat et al., 1986, "Large T Antigens of Simian Virus 40 and Polyomavirus Efficiently Establish Primary Fibroblasts." Journal of Virology, 59(3): 746-750.
GenBank accession No. EHB01992.1.

* cited by examiner

Primary Examiner — Anne Gussow
Assistant Examiner — Mindy G Brown
(74) Attorney, Agent, or Firm — Riverside Law LLP (57) ABSTRACT

Provided is a novel hyaluronan synthase (HAS2), isolated nucleic acids encoding it, and expression vectors which express the novel HAS2. Also provided are cell cultures which contain cells which harbor the expression vectors, methods of using the cell cultures to produce high molecular weight hyaluronic acid, and cell culture media that contains the high molecular weight hyaluronic acid.

4 Claims, 5 Drawing Sheets

COMPOSITIONS AND METHODS FOR RECOMBINANT SYNTHESIS OF HIGH MOLECULAR WEIGHT HYALURONIC ACID

CROSS-REFERENCE TO RELATED APPLICATIONS

This application is the U.S. national phase application filed under 35 U.S.C. §371 claiming benefit to International Patent Application No. PCT/US2013/024584, filed on Feb. 4, 2013, which is entitled to priority under 35 U.S.C. §119(e) to U.S. provisional application No. 61/594,929, filed Feb. 3, 2012, the disclosure of which is incorporated herein by reference in its entirety.

FIELD OF THE INVENTION

This invention relates to field of hyaluronic acid (HA) and more particularly to compositions and methods for recombinant synthesis of high molecule weight hyaluronic acid (HMWHA).

BACKGROUND OF THE INVENTION

HA is a non-sulfated glycosaminoglycan found in the extra cellular matrix of most cells, and increased amounts are found in connective, neural and epithelial tissues. Hyaluronic acid is made up of linear polymeric chains in which disaccharide units of N-acetylglucosamine and glucoronic acid, bonded via by glucoside bonds, are repeated. It has been reported to have roles in promoting contact inhibition through binding to the cell surface glycoprotein CD44. HA is widely used in supporting joint function in arthritis patients (such as via knee injections), beauty products, and veterinary medicine (knee injections for race horses). The currently commercially available HA is purified from bacteria or rooster combs. The cost of HA is 1-10 million dollars per kilogram, depending on the polymer length (the longer, more valuable). There is a need for improved compositions and methods for making HA, and particular, for making high molecular weight HA.

SUMMARY OF THE INVENTION

The present invention comprises compositions and methods for production of HMWHA. The compositions comprise isolated polynucleotides which encode a novel hyaluronan synthase (HAS). The HAS, referred to herein as HAS2, is of mole rat origin and can be characterized by Serine replacements of two Asparagines that are 100% conserved among mammalian HAS proteins. The amino acid sequence of the HAS2 that is a subject of the invention is presented in SEQ ID NO:1. The two amino acid replacements of Asn with Ser are designated by the Ser at positions 178 and 301 in SEQ ID NO:1.

The invention includes an isolated protein comprising or consisting of the sequence of SEQ ID NO:1, or a protein having at least 98% amino acid homology to it, provided the two replacements of Asn with Ser are included in the protein having at least 98% similarity to SEQ ID NO:1. In certain embodiments, the amino acid differences between the protein that has the 98% similarity and SEQ ID NO:1 comprise conservative amino acid substitutions, or insertions or deletions.

The invention also comprises all recombinant and isolated polynucleotides that comprise or consist of a polynucleotide sequence encoding the sequence of SEQ ID NO:1, including RNA and DNA sequences, and including all polynucleotides encoding a protein having at least 98% amino acid homology to SEQ ID NO:1.

A representative and non-limiting polynucleotide sequence which encodes the HAS2 of the invention is the cDNA presented in SEQ ID NO:2. In addition to a polynucleotide having the of SEQ ID NO:2, the invention includes polynucleotides that comprise the DNA complement of the cDNA, the mRNA equivalent of the cDNA, as well any isolated or recombinant polynucleotide which comprise a DNA sequence from which an mRNA encoding the amino acid of SEQ ID NO:1 can be transcribed.

The polynucleotides of the invention can be present in any suitable expression vector, many of which are commercially available. In certain embodiments, the expression vector is a mammalian expression vector configured to express a protein comprising the sequence of SEQ ID NO:1.

The invention further provides a population of cells comprising a recombinant or isolated polynucleotide encoding the amino acid sequence of SEQ ID NO:1. Such cells can be cultured and produce hyaluronic acid having a molecular weight of at least 6,000 kDa.

The invention also includes a method for obtaining high HMWHA producing cells which comprises transfecting cells with a polynucleotide encoding SEQ ID NO:1, and culturing the cells so that they produce HMWHA.

In another embodiment, the invention provides a conditioned medium which is obtained by incubating a population of cells which have been engineered to express HMWHA according to the invention in a culture medium for a period of time. The conditioned medium can be condition for any period between 3 hours and 30 days, and can be free of cells and/or cellular debris.

The invention also provides a composition comprising HMWHA that is produced by cells engineered to express the novel HAS2 that is a subject of the invention. Such HMWHA can be provided as a neutraceutical or pharmaceutical preparation.

The invention also provides a method of prophylaxis or therapy of a disorder in an individual in need of hyaluronic acid treatment comprising administering to the individual a composition comprising HMWHA produced by a method of the invention, wherein the disorder in the individual is prevented, inhibited from developing, or wherein symptoms of the disorder are alleviated.

BRIEF DESCRIPTION OF THE DRAWINGS

FIG. 1. Naked mole rat cells secret HA of exceptionally high molecular weight. (A) Naked mole rat cells make the culture media viscous. Viscosity of water, media, or media conditioned with human, mouse or naked mole rat fibroblasts for 20 days measured using Ostwald Viscometer. The last bar shows naked mole rat conditioned media digested with 1 U/ml HAase. The experiment was repeated three times; error bars show s.d. (B) Purified HA separated on pulse-field gel. The experiment was repeated five times, using both skin and lung fibroblasts, and a representative gel is shown. (C) Western blot sowing the levels of HAS synthases. (D) Conserved catalytic domain of mammalian HAS2 proteins. The top sequence (SEQ ID NO:3) is a catalytically active portion of the naked mole rat HAS2. Dots indicate amino acids identical to the naked mole rat sequence. The two amino acid changes unique to the naked mole rat are indicated by boxes. HSF, human skin fibroblasts; MSF, mouse skin fibroblasts; NMRSF, naked mole rat skin fibroblasts; NMR SF Mut, naked mole rat fibroblasts that lost ECI; NMR EF, embryonic naked mole rat fibroblasts that do not display ECI; HAase, enzyme that specifically digests HA.

FIG. 3. HMW-HA is required for ECI. (A) Cells grown in the presence of 3 U/ml HAase do not display ECI and proliferate to high cell density. (B) Quantification of cell growth data, showing the maximum cell number per plate achieved under indicated growth conditions. The last bar shows naked mole rat cells grown in the presence of 5 µg/ml CD44-blocking antibody. All experiments were repeated at least three times and error bars show s.d.; asterisk indicates P<0.001 by t-test. (C) Naked mole rat cells were grown in the presence of HAase for 12 days, then HAase was removed. (D) Naked mole rat cells capable of ECI express an additional CD44 isoform, compared to mutant naked mole rat cells and human cells. (E) Naked mole rat cells have higher affinity to HA. Cells were incubated with 35 µg/ml of fluorescently labeled HA and fluorescence was measured by flow cytometry. Experiment was repeated four times; error bars are s.e.m; P<0.001 by t-test. (F) Western blot showing in NF2 phosphorylation status and $p16^{Ink4a}$ levels in growing and confluent naked mole rat cells. HSF, human skin fibroblasts; MSF, mouse skin fibroblasts; NMRSF, naked mole rat skin fibroblasts; NMR SF Mut, naked mole rat fibroblasts that lost ECI; HAase, enzyme that specifically digests HA.

FIG. 5. A. Purified HA separated on pulse-field gel and stained with StainsAll solution. The experiment was repeated five times, using both skin and lung fibroblasts, and a representative gel is shown. B. Naked mole rat HAS2 protein expressed in human HEK293 cells secretes HMW-HA. HEK293 cells were transfected with an expression vector containing the HAS2 cDNA under CMV promoter and allowed to express HAS2 for 2 days, after which HA secreted into the media was analyzed by pulse-field gel (left panel). Control cells were transfected with GFP expression vector. The right panel shows a Western blot with HAS2 antibodies, confirming that HAS2 protein is overexpressed in HEK293 cells. Legend: HSF, human skin fibroblasts; MSF, mouse skin fibroblasts; NMRSF, naked mole rat skin fibroblasts; NMR SF Mut, naked mole rat fibroblasts that lost ECI; NMR EF, embryonic naked mole rat fibroblasts that do not display ECI; HAase, enzyme that specifically digests HA.

DESCRIPTION OF THE INVENTION

The present invention provides compositions and methods for synthesis of high molecular weight hyaluronic acid (HMW-HA). The invention is based in part on our studies on the naked mole rat, which is a small rodent known for its extreme longevity and low incidence of cancer. We believe we have identified a mechanism that is at least partly responsible for the naked mole rat's cancer resistance. This mechanism is related to our discovery of the ability of naked mole rat fibroblasts to secrete HMW-HA. This HMW-HA is over six times larger than human or mouse HA. We have now discovered that the synthesis of this HMW-HA is driven by a novel hyaluronan synthase. In connection with this, it is notable that hyaluronan synthases are highly conserved in vertebrates. However, when we cloned and sequenced HAS2 cDNA from the naked mole rat and compared it to other mammalian HAS2 genes, we discovered that the naked mole rat HAS2 has two Asparagines that are 100% conserved among mammals replaced with Serines (see FIG. 1D). This change occurs in no other mammalian HAS2 presently deposited in GenBank, including the naked mole rat's closes relative, the guinea pig. While not intending to be bound by any particular theory, it is believed that these unique amino acid changes are likely responsible for higher processivity of the naked mole rat HAS2, which results in synthesis of HMW-HA. The invention accordingly provides isolated polynucleotides encoding a mammalian HAS2 having a Ser at positions 178 and 301, expression vectors comprising the isolated polynucleotide sequences, compositions comprising cells into which such expression vectors have been introduced, methods for making HMW-HA using the compositions described herein, and isolated mammalian HAS2 protein comprising a Ser at positions 178 and 301.

Due to the highly conserved amino acid sequences of mammalian HAS2 proteins, with the exception of the two Asn→Ser replacements disclosed herein, it is expected that any mammalian HAS2 protein sequence and polynucleotide sequences encoding them are suitable for including in the invention, provided that the HAS2 protein has been modified to contain Ser at positions 178 and 301 (or the correlative positions in the sequence having at least 98% homology). In this regard, and in addition to the alignments depicted in FIG. 1D, we have determined that there is 98% identity between the naked mole rat HAS2 and mouse HAS2, as well as a 98% identity between the naked mole rat and the human HAS2 amino acid sequences. Therefore, it is expected that any mammalian HAS2 protein that has at least 98% similarity (homology) to the sequence of SEQ ID NO:1 will function in the invention, so long as the two Asn→Ser replacements are made in such non-naked mole rat HAS2 amino acid sequences. Thus, other known HAS2 sequences can be modified to contain a Ser at positions 178 and 301, and such HAS2 protein sequences and isolated polynucleotides encoding them are included in the invention. In certain embodiments, the amino acid differences between the protein that has the 98% similarity and SEQ ID NO:1 comprise conservative amino acid substitutions, or amino acid insertions or amino acid deletions. Non-limiting examples of amino acid substitutions contemplated in the present invention include, but are not limited to: gly or ser for ala; lys for arg; gln or his for asn; glu for asp; ser for cys; asn for gln; asp for glu; ala for gly; asn or gln for his; leu or val for ile; ile or val for leu; arg for lys; leu or tyr for met; thr for ser; tyr for trp; phe for tyr; and ile or leu for val. In the HAS2 proteins provided by the invention (and in the polynucleotide sequences that encode them) which differ from SEQ ID NO:1 by up to 2% in amino acid sequence, the proteins comprise the aforementioned Ser instead of Asn. In embodiments, the proteins are capable of producing HMW-HA. In certain embodiments, the amino acid homology to SEQ ID NO:1 comprises at least 98% homology to the HAS2 sequence depicted in FIG. 1D (SEQ ID NO:3), which is the segment of SEQ ID NO:1 from amino acid number 157 to amino acid number 321.

In one embodiment, the HAS2 protein produced by the methods disclosed herein and/or the isolated polynucleotide encoding such HAS2 proteins has a sequence obtained from a mammal belonging to family Bathyergidea, family Spalacidae, or family Geomyidae, but which have been engineered to have Ser at positions 178 and 301 (or corresponding amino acid locations in those HAS2 proteins, as the case may be). In one embodiment, the isolated HAS2 protein produced according to the invention and/or the isolated polynucleotide encoding it is obtained from the naked mole rat, which has the scientific name *Heterocephalus glaber*.

A representative sequence of a suitable HAS2 is presented in SEQ ID NO:1, which is the naked mole rat HAS2 protein sequence. The Ser at positions 178 and 301 are bold, enlarged and shaded. SEQ ID NO:1 is:

MHCERFLCILRIIGTTLFGVSLLLGITAAYIVGYQFIQTDNYYFSFGLYG

AFLASHLIIQSLFAPLEHRKMKKSLETPIKLNKTVALCIAAYQEDPDYLR

KCLQSVKRLTYPGIKVVMVIDGNSDDDLYMMDIFSEVMGRDKSATYIWKN

NFHEKGPGETDESHKESSQHVTQLVLS S KSVCIMQKWGGKREVMYTA

FRALGRSVDYVQVCDSDTMLDPASSVEMVKVLEEDPMVGGVGGDVQILNK

YDSWISFLSSVRYWMAFNIERACQSYFGCVQCISGPLGMYRNSLLHEFVE

DWY S QEFMGNQCSFGDDRHLTNRVLSLGYATKYTARSKCLTETPIEY

LRWLNQQTRWSKSYFREWLYNAMWFHKHHLWMTYEAVITGFFPFFLIATV

IQLFYRGKIWNILLFLLTVQLVGLIKSSFASCLRGNIIMVFMSLYSVLYM

SSLLPAKMFAIATINKAGWGTSGRKTIVVNFIGLIPVSVWFTILLGGVIF

TIYKESKKPFSESKQTVLIVGTLLYACYWVMLLTLYVVLINKCGRRKKGQ

QYDMVLDV

Any HAS2 amino acid sequence having at least 98% homology to SEQ ID NO:1 and polynucleotide sequences encoded such HAS2's are included in the invention, provided they are designed so that there is a Ser at positions 178 and 301.

A representative polynucleotide sequence (cDNA) encoding the polypeptide of SEQ ID NO:1 is presented in SEQ ID NO:2, although the invention includes all polynucleotide sequences which can encode the amino acid sequence of SEQ ID NO:1.

SEQ ID NO:2 is:

ATGCATTGTGAGAGGTTTCTATGTATCCTGAGAATAATTGGAACCACGCT

TTTTGGAGTCTCTCTTCTCCTTGGAATCACAGCTGCTTATATCGTTGGCT

ACCAGTTTATCCAAACGGACAATTACTATTTCTCTTTTGGATTATATGGT

GCCTTTTTAGCATCACATCTCATCATCCAAAGCCTATTTGCCTTTTTGGA

ACACAGGAAATGAAAAAATCTCTAGAAACCCCCATTAAGTTGAACAAA

CTGTTGCTCTTTGCATCGCTGCATATCAAGAAGACCCAGACTACTTACGA

AAATGTTTGCAATCTGTGAAAAGGCTCACCTACCCCGGGATTAAGGTTGT

CATGGTCATAGATGGGAACTCGGATGATGACCTGTACATGATGGACATCT

TCAGCGAAGTCATGGGCAGGGACAAGTCAGCCACTTACATCTGGAAAAAC

AACTTCCACGAAAAGGGTCCTGGTGAGACGGATGAGTCACATAAAGAGAG

CTCACAGCACGTGACACAGTTGGTCTTGTCCAGTAAAAGTGTGTGCATCA

TGCAAAAGTGGGGTGGAAAACGAGAAGTCATGTACACAGCCTTCCGAGCC

CTGGGACGAAGTGTGGATTATGTGCAGGTTTGTGACTCCGATACCATGCT

GGACCCTGCCTCATCTGTGGAGATGGTGAAAGTTTTAGAAGAAGACCCCA

TGGTTGGAGGAGTTGGGGGGGATGTCCAGATTTTAAACAAGTATGATTCC

TGGATCTCTTTCCTCAGCAGTGTGAGATACTGGATGGCTTTTAATATAGA

AAGGGCCTGTCAGTCGTATTTTGGGTGTGTCCAGTGCATCAGTGGACCTC

TGGGAATGTACAGAAACTCCCTGCTGCATGAGTTTGTGGAAGACTGGTAC

AGTCAAGAATTCATGGGCAACCAGTGTAGTTTTGGAGATGACAGGCACCT

AACAAATCGGGTGCTGAGTCTGGGCTATGCCACAAAATACACAGCTCGGT

CCAAGTGCCTTACTGAAACACCAATCGAATATCTCAGATGGTTGAACCAG

CAGACCCGTTGGAGCAAGTCCTACTTCCGAGAGTGGCTGTACAATGCAAT

GTGGTTCCACAAGCATCACTTGTGGATGACCTATGAAGCAGTCATCACTG

GATTTTTCCCTTTCTTTCTCATTGCCACAGTAATCCAGCTCTTCTACAGG

GGGAAAATTTGGAACATCCTTCTCTTCTTGCTAACTGTCCAGCTGGTAGG

GCTCATAAAATCATCTTTTGCCAGCTGCCTCAGAGGAAACATCATCATGG

TCTTTATGTCTCTCTACTCAGTGTTGTATATGTCAAGTTTACTTCCTGCC

AAAATGTTTGCAATCGCAACAATAAACAAAGCTGGGTGGGGCACATCCGG

AAGGAAAACCATTGTTGTCAACTTCATAGGACTCATCCCAGTGTCAGTTT

GGTTTACAATTCTCCTGGGTGGTGTGATTTTCACCATTTATAAGGAATCT

AAAAAGCCATTTTCTGAATCCAAACAGACAGTTTTAATTGTTGGAACATT

GCTCTATGCATGCTATTGGGTCATGCTGTTGACACTGTACGTGGTTCTCA

TCAATAAGTGTGGCAGGCGGAAGAAAGGACAGCAGTATGACATGGTGCTG

GACGTATGA

The polynucleotides encoding the HAS2 of the invention can be present in an expression vector. "Expression vector" refers to a vector comprising protein expression control sequences operatively linked to the HAS2 coding sequence. The expression vector can comprise cis-acting elements for expression, including but not limited to promoter elements, enhancer elements, origins of replication, selectable markers, transcription initiation sites, sequences that encode translation initiation sites, and any other sequence that is desirable for protein expression, depending on the expression system chosen; other elements for expression can be supplied by the host cell or in an in vitro expression system. Thus, recombinant expression vectors comprising polynucleotide sequences encoding the HAS2 protein disclosed herein are included in the invention, as are cell populations into which such recombinant expression vectors have been introduced. The expression vectors can be introduced into cells using any suitable technique, such as by transfection of eukaryotic cells. The transfections can be transient, or they can be such that the sequence encoding the novel HAS2 protein of the invention is integrated into a chromosome, or maintained as an episomal element. Suitable protein expression vectors which can be designed to include the polynucleotide sequences of the invention and express the HAS2 protein include all those known in the art, examples of which include but are not limited to cosmids, plasmids and virus-based systems that incorporate the recombinant polynucleotide encoding the HAS2. The system used to express the recombinant HAS2 proteins of the invention can be any suitable organism or in vitro protein expression system. Suitable expression systems that utilize organisms and/or viruses include but are not limited to mammalian cell expression systems, insect cell expression systems (e.g., baculovirus-based systems), yeast expression systems, and prokaryotic expression systems. Suitable expression vectors and expression systems can be made using commercially available reagents. In one embodiment, the invention includes a population of eukaryotic cells comprising a recombinant expression vector encoding an HAS2 protein described herein. In one embodiment, the eukaryotic cells are mammalian cells.

HMW-HA can be produced using the recombinant expression systems described herein or those that are otherwise apparent to those skilled in the art given the benefit of the present disclosure, or commercially available systems engineered to express the HAS2 described herein. The HMW-HA is an unbranched disaccharide glucuronic acid/N-acetylglucosamine polymer and is one of the major components of the extracellular matrix. Biological responses triggered by HA depend on the HA polymer length. HMW-HA represses mitogenic signaling and has anti-inflammatory properties, while low molecular weight HA promotes proliferation and inflammation.

In one aspect, the invention provides a method for making HMW-HA wherein the molecular weight of HA is greater than 6,000 kDa as determined on agarose gel electrophoresis. In various embodiments, the molecular weight of the HA is greater than 7,000, 8,000, 9,000 and 10,000 kDa (including molecular weight in kDa of all integers between 6,000 and 10,000). Thus, when a reference is made to a high molecular weight hyaluronic acid, it means HA which has a molecular weight of at least 6,000 kDa.

HMW-HA made using the expression systems which comprise polynucleotides encoding the novel HAS2 described herein can be purified from the expression system using any suitable technique, method and/or apparatus. In one embodiment, the HMW-HA is secreted into media by cells into which an expression vector described herein has been introduced. Thus, in one embodiment, the invention provides cell culture media which contains the HMW-HA. The invention also includes compositions comprising HMW-HA that has been separated from, for example, conditioned media in which cells which express the HAS2 of the invention are cultured. The conditioned media can be, for example, treated with proteases, ethanol precipitation, resuspension of the precipitate in buffer and gel The HMW-HA can be purified to any desirable degree of purity. The conditioned media obtained from the cells should be processed under sterile conditions or sterilized as needed. When appropriate (i.e., once the medium is conditioned so that hyaluronic acid or some other marker such as growth factors have reached desirable levels in the medium) the "conditioned" medium can be collected. In one embodiment, the conditioned media can be collected anytime from 3 hours to 30 days of conditioning (i.e., after plating cells which express the recombinant HAS2 as described herein). In one embodiment, the conditioned medium is collected after 2, 3, 6, 12, 18, 24, 30, 36, 42, 48 hours, 3, 4, 5, 10, 15, 20, 25 or 30 days and all days and hours therebetween, and all ranges of time between 2 hours and 30 days. In one embodiment, it is collected anytime between 2 hours and 60 hours of incubation.

The recombinant cell-derived conditioned medium is unique in that it contains a high level of high molecular weight hyaluronic acid. Therefore in one embodiment, this invention provides a neat (unprocessed) conditioned medium from the cells provided herein or partially or fully purified fractions of the medium comprising high molecular weight hyaluronic acid. In one embodiment, the conditioned medium from the cells comprises at least 50 ng/ml of HA having a molecular weight of at least 6,000 kDa. In various embodiments, the conditioned medium has at least 50 ng to 5 mg/ml of HMW-HA and all integer values and ranges in nanograms therebetween. In various embodiments, one ml of conditioned medium has at least 50, 100, 200, 300, 400, 500, 600, 700, 800, 900 ng, 1, 1.5, 2, 2.5, 3, 3.5, 4, 4.5, 5 μg of HMW-HA. In another embodiment, one ml of conditioned medium has 1 to 5 μg of HMW-HA.

If desired, the conditioned medium can be processed to concentrate selected components. For example, the medium may be concentrated 10 to 20 fold using a positive pressure concentration device (such as a device having a filter with a 0.2 or 0.45 μm cut-off (Amicon, Beverly, Mass.). Also, the conditioned medium may be further processed for HA isolation and purification to remove unwanted proteases. The conditioned medium with or without processing can be used fresh or can be stored (at refrigerator or freezer temperatures) for later use.

Accordingly, in one aspect of the invention, the invention provides conditioned medium that has previously supported the growth of cells which comprise an expression vector as described herein.

The HMW-HA produced by the compositions and methods of the present invention can be used in various pharmaceutical, neutraceutical, therapeutic or any other type of formulation that will come in contact with an individual or will be administered to an individual via any route of administration. Examples include but are not limited to medications for injection in arthritic joints, veterinary medicine, dietary supplement, and in cosmetics in creams and anti-wrinkle injections. Thus, in one aspect, the present invention provides neutraceutical and/or pharmaceutical formulations comprising, consisting essentially of, or consisting of HMW-HA made using the compositions and methods of the present invention. In certain embodiments, the invention includes making a pharmaceutical or neutraceutical composition which comprises culturing cells engineered to express HMW-HA according to the invention, separating HMW-HA from the culture medium, and combining the separated HMW-HA with a carrier, excipient, stabilizer, or any other pharmaceutical and/or neutracueutical agent to provide the pharmaceutical or neutraceutical composition. Either or both of the pharmaceutical and neutraceutical composition can be used to impart to an individual an effect including but not necessarily limited to a cosmetic, health, prophylactic, or therapeutic benefit. In certain embodiments, the compositions of the invention can be used to improve the general well-being of an individual.

The present invention also provides a method of alleviating a medical condition (which can be alleviated by administration of HMW-HA) by administration of HA to an individual. The individual can be an individual in need of HA treatment, or suspected of having, or at risk for developing a disorder where HA treatment would be of benefit. Thus, the invention provides for prophylaxis and therapeutic uses of HA.

With respect to the naked mole rats that we studied, their normal habitat is in large subterranean colonies in Africa. The colonies have a eusocial structure with one breeding queen, similar to ants and bees. The naked mole rat displays exceptional longevity, with a maximum lifespan exceeding 30 years. This is the longest lifespan for a rodent species, and is especially striking, considering the small, approximately 35 g, body mass of the naked mole rat. In comparison, a similarly sized house mouse has maximum lifespan of 4 years. In addition to their longevity, naked mole rats show an unusual resistance to cancer. Multi year observation of a colony of 800 animals did not identify a single incidence of cancer. Previous studies identified a novel anticancer mechanism in the naked mole rat termed early contact inhibition (ECI). Contact inhibition is a process of arresting cell growth when cells come in contact with each other or extracellular matrix. Contact inhibition is a powerful anticancer mechanism that is lost in cancer cells. Naked mole rat cells arrest at a much lower density than mouse cells, and the loss of the ECI makes cells more susceptible to malignant transformation. However, the upstream signals triggering ECI remained unknown.

Figure 1:
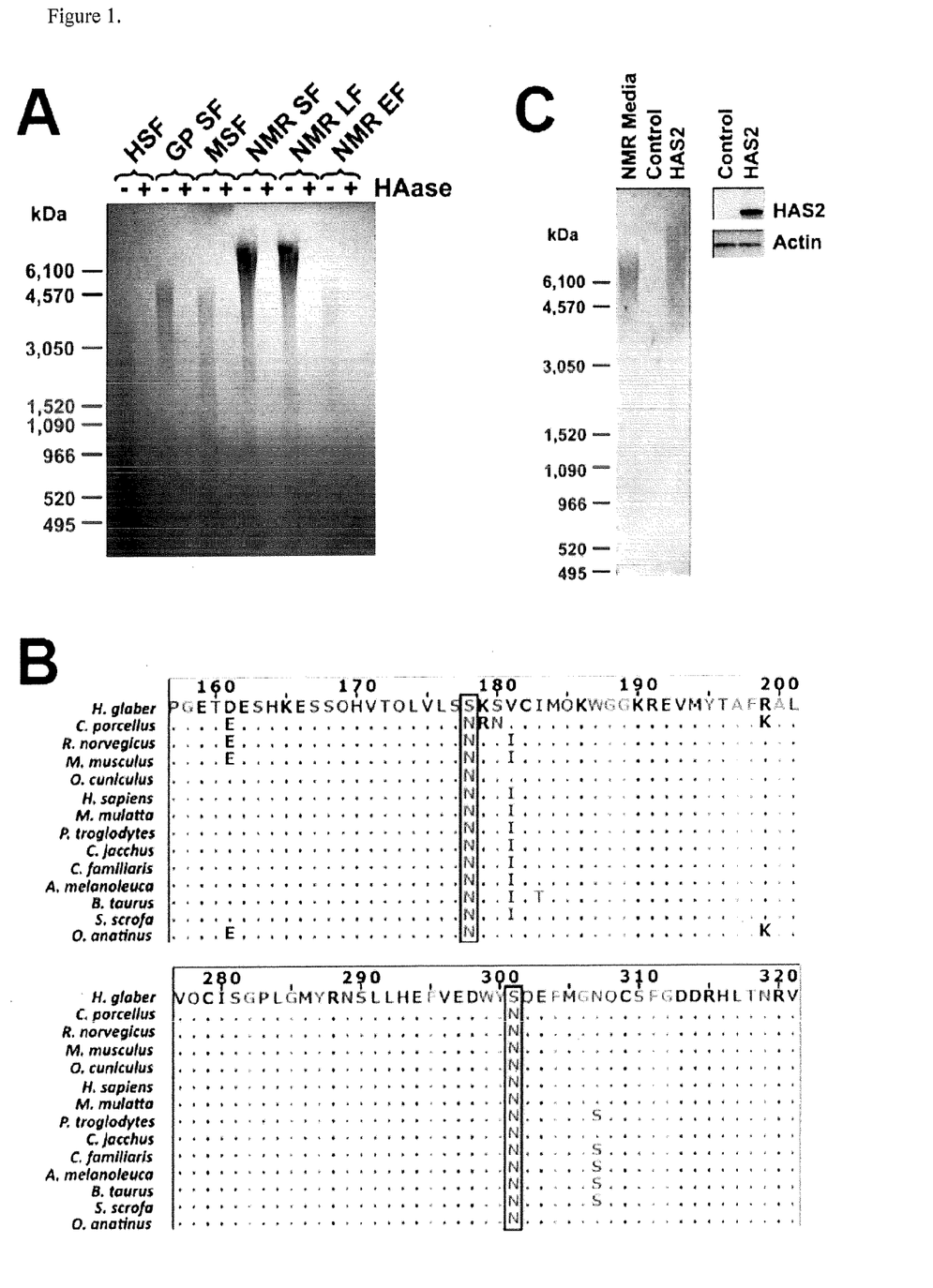

While culturing multiple lines of naked mole rat fibroblasts we noticed that the culture media on the plates became very viscous after a few days of culture, frequently clogging the vacuum systems used to aspirate the media. Viscosity measurements confirmed that the media conditioned by the naked mole rat cells was more viscous than the media conditioned by human or mouse cells (FIG. 1A). We identified the viscous "substance" secreted by the naked mole rat fibroblasts as high molecular weight HA (HMW-HA). Treatment with an enzyme hyaluronidase (HAase) that specifically digests HA, reduced the media viscosity to the background levels (FIG. 1A).

As noted above, we cloned and sequenced HAS2 cDNA from the naked mole rat and compared it to other mammalian HAS2 genes (FIG. 1D). In addition to the description of the amino acid sequence of HAS2 discussed above, it is noteworthy that HAS2 contains seven putative transmembrane domains and a long cytoplasmic loop. The conserved regions carrying Asparagine to Serine replacements correspond to putative cytoplasmic loop containing the enzyme's active site. Thus, these unique amino acid changes may be responsible for higher processivity of the naked mole rat HAS2.

Figure 2:
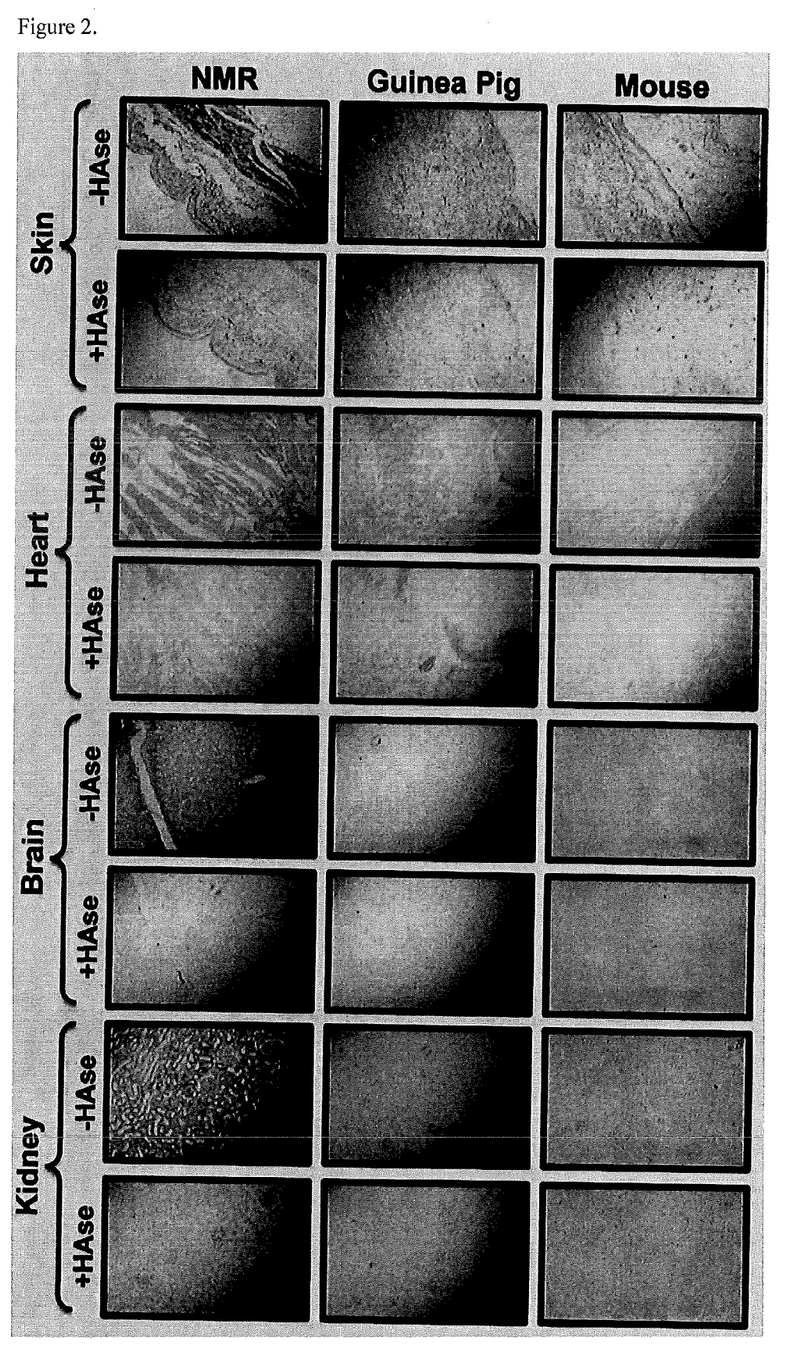
FIG. 2. Naked mole rat tissues contain high levels of HA. Tissues from the naked mole rat, mouse, and guinea pig were stained with Alcian Blue pH 2.5. The control samples treated with HAase do not show blue staining, demonstrating that the staining is specific to HA. Staining was performed on three different animals and representative images are shown.

We then examined whether naked mole rat tissues contain high levels of HMW-HA. Naked mole rat tissues were compared to mouse and guinea pig. We included the guinea pig because it is phylogenetically closer to the naked mole rat than the mouse. Tissue sections were stained with alcian blue, and control samples were treated with HAase prior to staining to show that the staining is specific to HA. Naked mole rat skin, heart, brain, and kidneys were highly enriched for HA (FIG. 2). This result indicates that secretion of the very high HMW-HA by naked mole rat cells is not an artifact of tissue culture, but a unique in vivo property of this species, serving a physiological role.

Figure 3:
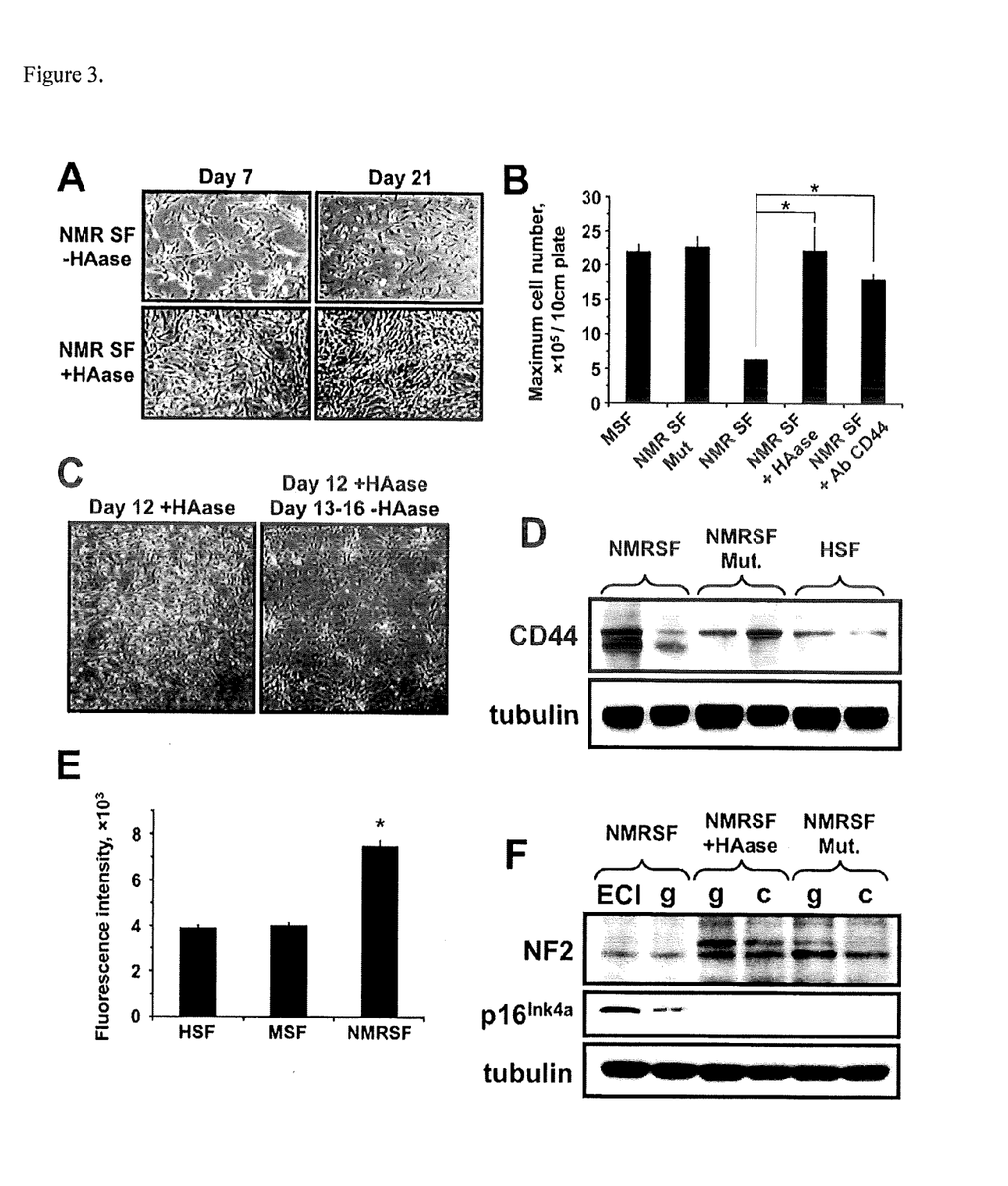

We previously demonstrated that ECI contributes to the cancer resistance of the naked mole rat by arresting cell cycle via induction of p16INK4a. To determine the role of HMW-HA in ECI we cultured naked mole rat fibroblasts in the presence of bacterial hyaluronidase (HAase), an enzyme that specifically cleaves HA into short fragments. Enzymatic digestion of HMW-HA reduced the levels of p16INK4a (FIG. 3E), abrogated the ECI phenotype and caused naked mole rat cells to grow to complete confluence (FIG. 3A, B). Upon subsequent removal of HAase from the culture media, a fraction of cells detached from the plate and died, while the remaining cells "pushed away" from each other and re-acquired the ECI phenotype (FIG. 3B, C). Importantly, a mutated clone Mut-NMR-SF2, which spontaneously lost the ECI phenotype and p16 expression, still produced HMW-HA (FIG. 1B), indicating that the physical presence of HMW-HA is not sufficient for the ECI phenotype; rather the intact signaling pathway leading from HMW-HA to induction of p16 is required. These experiments establish HMW-HA as the extracellular signal that triggers ECI.

CD44 is a major HA receptor in human and mouse cells. To confirm that HA signaling triggering ECI occurs via the CD44 receptor we cultured naked mole rat cells in the presence of a CD44-blocking antibody. Naked mole rat cells grown with CD44 antibodies reached higher cell density (FIG. 3B) indicating that the ECI signal from HMW-HA is transmitted via the CD44 receptor.

Interestingly, naked mole rat cells capable of undergoing ECI displayed an additional isoform of CD44 receptor compared to Mut-NMR-SF2 cells or to human cells (FIG. 3D). We then used Flow cytometric assay to measure the affinity of the naked mole rat cells to fluorescently labeled HA. Naked mole rat cells displayed higher affinity to HA than mouse or human cells (FIG. 3E).

On the cytoplasmic face, the CD44 receptor interacts with NF2 (merlin), which transmits the signal from HA. Unphosphorylated merlin is a negative growth regulator. Phosphorylated merlin appeared in naked mole rat cells grown in the presence of HAase, while cells in standard conditions contained only the unphosphorylated growth-inhibitory form of merlin (FIG. 3F). Collectively these results establish that ECI is signaled via the HA/CD44/merlin pathway.

Figure 4:
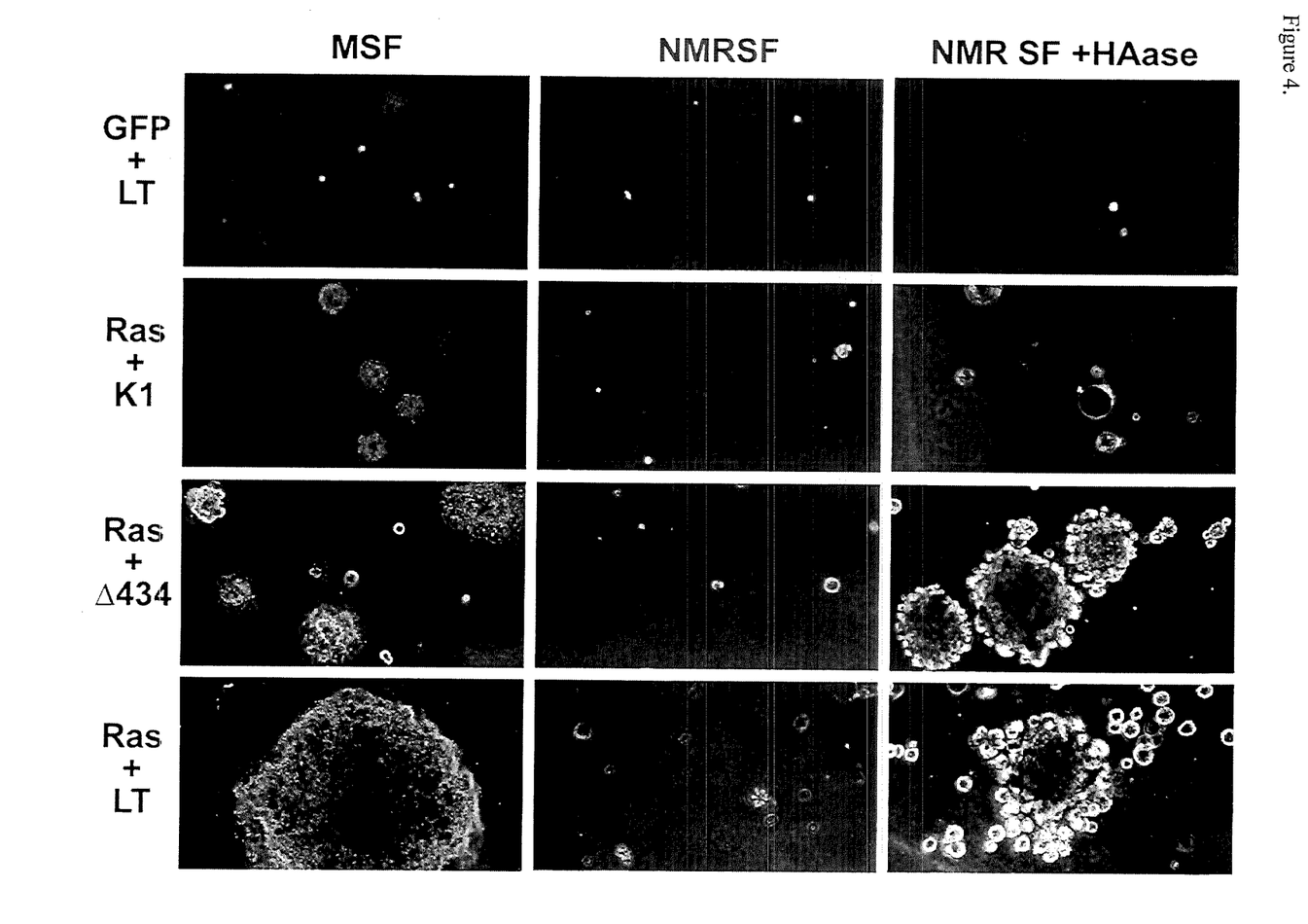
FIG. 4. Removal of HMW-HA makes naked mole rat cells susceptible to anchorage-independent growth. Cells were transfected with vectors encoding SV40 LT or its mutant derivatives and oncogenic Ras, and plated in soft agar. Cells were cultured with or without HAase. The image shows colonies after 3 weeks of growth at 20× magnification. The experiment was repeated three times.

We then tested the role of HMW-HA in the resistance of naked mole rat cells to malignant transformation in a soft agar assay. A combination of H-Ras V12 and SV40 LT or LTΔ434-444 is sufficient to transform mouse fibroblasts, but as we showed earlier is not sufficient to confer anchorage independent growth to naked mole rat cells. To test the role of HMW-HA in the naked mole rat's resistance to transformation, we transfected naked mole rat fibroblasts with H-Ras V12 combined with SV40 LT or its mutants LTK1 or LTΔ434-444 and cultured them in soft agar in the presence of HAase. HAase was changed daily to ensure efficient digestion of HMW-HA. Under these conditions cells transfected with H-Ras V12 and SV40 LT, or H-Ras V12 and LTΔ434-444 formed robust colonies in soft agar (FIG. 4). This result demonstrates that if HMW-HA is degraded by HAase, naked mole rat cells become susceptible to transformation by H-Ras V12 and SV40 LT. This experiment establishes HMW-HA as a key component responsible for elevated cancer resistance of the naked mole rat.

Figure 5:
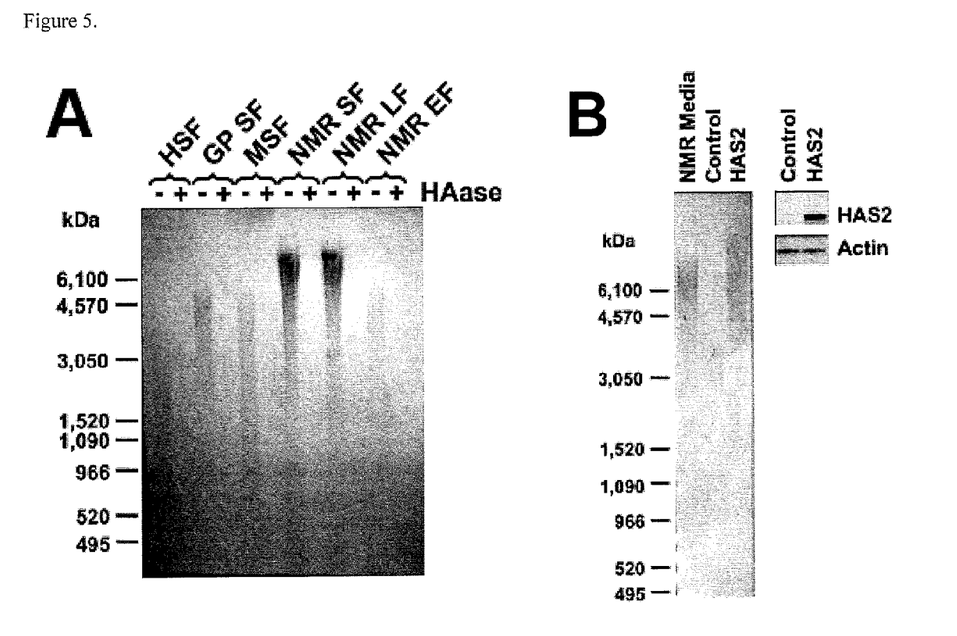

To demonstrate cloning and expression of functional naked mole rat HAS2 in an illustrative recombinant expression system as generally described above, the HAS2 cDNA (SEQ ID NO:2) was cloned in pEGFP-N1 mammalian expression vector (CLONTECH) under CMV promoter control; the cDNA replaced EGFP. FIG. 5A shows a photographic representation of results demonstrating purified HA separated on pulse-field gel and stained with StainsAll solution. We transfected the engineered expression vector described above into human HEK293 cells. As can be seen from FIG. 5B, right panel, the cells expressed the HAS2 protein (comprising SEQ ID NO:1). We cultured the transfected cells for two days, separated the cells from the culture media, and analyzed HA in the culture media by pulse-field gel analysis. A photographic representation of the pulse-field gel analysis is shown in FIG. 5B, left panel, and confirms HMW-HA production and secretion by the transfected cells. Control cells were transfected with a GFP expression vector and do not produce detectable HMW-HA in the assay. Thus, we have demonstrated at least the following: i) an isolated polynucleotide encoding the novel HAS2 disclosed herein; ii) isolated HAS2 protein; iii) a recombinant expression vector which comprises a polynucleotide sequence encoding the novel HAS2 disclosed herein; iv) a cell culture comprising cells harboring the recombinant expression vector; v) expression of the novel HAS2 from the expression vector in a mammalian cell culture; vi) production of HMW-HA from the cells in the cell culture; and vii) separation of the HMW-HA from the cell culture media.

In summary, our results demonstrate that the novel HAS2 we discovered can be produced recombinantly, and can function in mammalian cells to produce HMW-HA, and that the HMW-HA can be recovered from cell culture media. Further, we demonstrate that HMW-MAA and its increased affinity for the CD44 receptor play a key role in cancer resistance of the naked mole rat and therefore may have the same or similar benefits for beneficial uses in humans.

The following materials and methods were used to obtain data presented in this disclosure.

Materials and Methods Animals.

Naked mole rats were from colonies from the University of Rochester colony. C57BL/6 mice were obtained from Charles River Labs. Non-albino guinea pigs were obtained from Elm Hill Labs. Cells and tissues were obtained from at least three different animals.

Cell Culture.

Primary mouse and naked mole rat cells were isolated from lung and under arm skin. Cells were obtained from five naked mole rats and three mice. The growth characteristics, and HA secretion did not differ between the cell lines from different animals therefore we performed the experiments on three skin cell lines from three animals. All cell lines were used at early passage (<12-15 PDs).

Mouse cells were cultured at 37° C., 5% $CO_2$, 3% $O_2$; naked mole-rat cells were cultured at 32° C., 5% $CO_2$, 3% $O_2$ on treated polystyrene culture dishes (Corning) in EMEM media (ATCC) supplemented with 15% fetal bovine serum (Gibco), nonessential amino acids, sodium pyruvate, 100 units/ml penicillin, and 100 µg/ml streptomycin (Gibco).

Viscosity Assay.

To determine relative kinematic viscosity, 3 ml of distilled $H_2O$, unused complete EMEM media, or media conditioned with naked mole rat, mouse, or human cells were run through a 0.6 mm capillary Ostwald viscometer (Barnstead International) at 22° C. and timed for the passage of the media or distilled $H_2O$ through the capillary. For HAase control, naked mole rat media was treated with hyaluronidase; 1 U/ml HAase from *Streptomyces hyalurolyticus* (Sigma-Aldrich). Relative viscosities of unused and conditioned media was determined by comparing times required to pass through the capillary to that of distilled $H_2O$. Samples were run three times to determine an average relative viscosity.

Cell Growth Analysis.

To measure cell proliferation and the confluent density cells were seeded on 60 mm grided plates (Corning). Three 2×2 mm squares were marked on each plate and the number of cells in those squares was counted each day for 20 days. For cell growth in the presence of HAase, 24 hours post plating the media was changed to the media containing 3 U/ml HAase (Sigma). Media was then replaced with fresh media containing the enzyme every 48 hours. Images of the squares were taken using SPOT Advanced (Diagnostic Instruments) and analyzed using the colony counting program on ImageQuant TL (GE). The average count of the three squares for each day was multiplied by 458.33 to give the total cell count per 10 cm plate. Cell count data was analyzed using Microsoft Excel.

Pulse Field Gel Electrophoresis.

HA in Day 20 conditioned media were determined using pulse field gel electrophoresis. HA was purified from conditioned media by first 2 ml of conditioned media with 500 µg of Proteinase K (Roche) at 50° C. for 45 minutes to remove proteins. Samples were then precipitated by adding 2 ml of 100% ethanol. The pellet was dissolved in 500 µl TE Buffer and incubated overnight at 4° C. The following day, aliquots were removed and treated with hyaluronidase from *Streptomyces hyalurolyticus* (Sigma-Aldrich). Twenty-five µl of each sample was mixed with 5 µl 4M sucrose loading solution and loaded to a 0.4% pulse field SeaKem Gold agarose gel (Cambrex). Ten µl of HA molecular size markers; HiLadder (~500 kDA to ~1,500 kDa) and Mega-A Ladder (1,500 kDa to 6,000 kDa) (from Hyalose) were run to determine the size of HA from each sample. Samples were run overnight at 4° C. at 75 volts with a 1 to 10 running ratio in TAE buffer. The gel was next stained in a method adapted from a known method. Briefly, the gel was placed in a 0.005% (w/v) Stains-All (Sigma-Aldrich) in 50% ethanol solution overnight. To destain, the gel was placed in distilled $H_2O$ for 48-hours and then placed under ambient light in distilled $H_2O$ for 4 hours to complete the final de-staining stages and then photographed under white light.

Antibodies.

The following antibodies were used: HAS1 (ab104864 Abcam; sc-23145 Santa Cruz), HAS2 (sc-66916 Santa Cruz), HAS3 (sc-66917 Santa Cruz), Elastin (ab77804 Abcam), α-tubulin (ab4074 Abcam), CD44 (217594 Calbiochem, ab41478 Abcam, ab24504 Abcam, ab51037 Abcam), NF2/Merlin (ab2478 Abcam, ab88957 Abcam, ab30329 Abcam, ab47378 Abcam), p16 (ab14244 Abcam, ab17517 Abcam), p27 (2552 Cell Signaling; DCS-72.F6 Lab Vision), Myosin Phosphatase (ab24670 Abcam), and γ-PAK (sc-1872 Santa Cruz).

Tissue Staining.

HA detection in tissues was done as follows. Tissue samples from young animals (3 year old naked mole rats, 3-5 months old mice, 1 year old guinea pigs) were fixed in 10% buffered neutral formalin, embedded in paraffin and quadruple sections cut at 5 µm were mounted on glass slides. Slides were deparaffinized and hydrated in distilled $H_2O$. They were then placed in Coplin jars containing 40 ml of hyaluronidase digestion solution (40 U hyaluronidase from *Streptomyces hyalurolyticus* (Sigma) in 40 mL of PBS) for the samples to be digested or in 40 ml of PBS for the non-digested samples. The jars were microwaved for one minute at 60 W and then transferred to a 37° C. oven for 1 hour. The slides were rinsed four times in distilled $H_2O$, followed by three rinses with 3% acetic acid. Next, slides were placed in new Coplin jars containing 1.0% filtered alcian blue solution (Alcian Blue 8GX, C.I. 74240 (Leica) in 3% acetic acid and microwaved at 60 W for 3 minutes followed by an additional 5 minute incubation in the hot 1.0% alcian blue solution. Slides were rinsed three times in distilled $H_2O$, dehydrated in graded alcohols and rinsed three times in xylene. Images were taken by light microscopy.

Naked Mole Rat Cell Growth Assays with CD44 Antibody.

Naked mole rat cells were seeded 50 cells/square onto cell culture treated 6 cm polystyrene gridded tissue culture plates (Corning). Twenty-four hours post plating; the media was changed to contain 5 µg/ml of CD44 specific antibody (Monoclonal Mouse $IgG_{2A}$ Clone #2C5, Catalog Number BBA10, R&D Systems) or no antibody control. Media was changed every 24-hours and images taken daily using SPOT Advanced imaging software (Diagnostic Instruments). Images from three different squares from two independent plates were counted from both the CD44 antibody treated or control groups.

HA Affinity Assay.

Naked mole rat and mouse cells were harvested at subconfluent exponential phase. One hundred thousand ($10^5$) cells of each type were incubated for 45 min on ice in 210 µl PBS containing 1.5% Fetal Calf Serum and 35 µg/ml fluorescein-labeled HA (Fluorescein-Labeled HA from Bovine Trachea, sc-221733, Santa Cruz Biotech, Santa Cruz, Calif.). Five thousand cells from each replicate were analyzed by FACS. The experiment was repeated four times.

Transfections.

Naked mole-rat skin fibroblasts were seeded at $2 \times 10^5$ cells/100 mm plate seven days prior to transfection. Mouse skin fibroblasts were seeded at $5 \times 10^5$ cells/100 mm plate three days prior to transfection. For transfection, cells were harvested, counted and $10^6$ cells were transfected with 5 mg of plasmid DNA using Amaxa Nucleofector II on program U-020 and solution NHDF (Amaxa). After transfection, cells were seeded at $2 \times 10^5$ live cells per 10 cm plate for apoptosis analysis and $7 \times 10^4$ live cells per 6 cm grid plates (Corning) for cell growth analysis in the same media as stated above. Media was replaced 24 hours post transfection to remove dead cells due to electroporation. Transfections included a mock with no DNA, pEGFP-N1 (Clontech), pSG5 Large T (Addgene 9053), pSG5 Large T K1 (Addgene 9055), pSG5 Large TΔ434-444 (Addgene 9054), and a no electroporation control.

Anchorage-Independent Soft Agar Growth Assay.

One million mouse, naked mole-rat wild type and naked mole-rat mutant exponentially growing skin fibroblast cells were transfected by Amaxa with the following plasmid DNA mixtures: 5 μg pEGFP-N1 (Clontech) and 5 μg pSG5 Large T, 5 μg pRas-V12 (Clontech) and 5 μg pSG5 Large T, 5 μg pRas-V12 and 5 μg pSG5 Large T K1, or 5 μg pRas-V12 and 5 μg pSG5 Large T Δ434-444. After transfection, cells were seeded and allowed to recover for 24 hours on 10 cm treated polystyrene plates (Corning) in 1× Minimum Essential Medium, Eagle with Earle's Balances salt Solution supplemented with 15% fetal calf serum and antibiotics (Gibco). The following day, a 2 ml final solution of 0.5% Difco Agar Noble (BD Bioscience) and 1× media mixture was poured into 6 cm treated polystyrene plates (Corning) and allowed to solidify in incubators at 37° C. After harvesting and counting cells transfected 24 hours previous, 50 to 50,000 cells were serially diluted and resuspended in 1 ml of 2× media. This cell suspension was then quickly mixed with 1 ml 0.7% liquid Difco Agar Noble, making a final 0.35% agar/1× media solution, and seeded on top of the solidified 0.5%/1× media. Plates were incubated at 32° C., 5% $CO_2$, ad 3% $O_2$ for twenty-four hours before the addition of 1 ml of EMEM media with or without hyaluronidase (HAse) from *Streptomyces hyalurolyticus* (Sigma) at 3 U/ml. Cells were grown for six weeks, with the removal of old liquid EMEM media and the addition of 1 ml of new EMEM with or without 3 U/ml HAse every 48 hours. Plates were monitored every 48 hours and photographed at week 3 and week 6 after plating at 200× on a Nikon TS100 phase contract microscope using SPOT software (Diagnostic Instruments).

This invention has been described through examples presented above. Routine modifications to the methods and compositions presented herein will be apparent to those skilled in the art and are intended to be within the scope of the claims appended hereto.

We claim:

1. A population of eukaryotic cells comprising a recombinant expression vector encoding a protein, wherein the protein comprises an amino acid sequence having at least 98% amino acid homology to the sequence of SEQ ID NO:1, wherein the amino acid sequence comprises a serine at amino acid positions 178 and 301 relative to the sequence of SEQ ID NO: 1.

2. The population of eukaryotic cells of claim 1, wherein the cells are present in an in vitro cell culture.

3. The population of eukaryotic cells of claim 2, wherein culture medium in which the cells are cultured comprises hyaluronic acid having a molecular weight of at least 6,000 kDa.

4. The population of eukaryotic cells of claim 1, wherein the protein comprises an amino acid sequence consisting of the sequence of SEQ ID NO:1.

* * * * *

SEQUENCE LISTING

```
<160> NUMBER OF SEQ ID NOS: 3

<210> SEQ ID NO 1
<211> LENGTH: 552
<212> TYPE: PRT
<213> ORGANISM: naked mole rat

<400> SEQUENCE: 1

Met His Cys Glu Arg Phe Leu Cys Ile Leu Arg Ile Ile Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Asp Asp Asp Leu
        115                 120                 125

Tyr Met Met Asp Ile Phe Ser Glu Val Met Gly Arg Asp Lys Ser Ala
    130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
                165                 170                 175

Ser Ser Lys Ser Val Cys Ile Met Gln Lys Trp Gly Gly Lys Arg Glu
            180                 185                 190
```

Val Met Tyr Thr Ala Phe Arg Ala Leu Gly Arg Ser Val Asp Tyr Val
          195                 200                 205

Gln Val Cys Asp Ser Asp Thr Met Leu Asp Pro Ala Ser Ser Val Glu
210                 215                 220

Met Val Lys Val Leu Glu Glu Asp Pro Met Val Gly Val Gly Gly
225                 230                 235                 240

Asp Val Gln Ile Leu Asn Lys Tyr Asp Ser Trp Ile Ser Phe Leu Ser
              245                 250                 255

Ser Val Arg Tyr Trp Met Ala Phe Asn Ile Glu Arg Ala Cys Gln Ser
                  260                 265                 270

Tyr Phe Gly Cys Val Gln Cys Ile Ser Gly Pro Leu Gly Met Tyr Arg
              275                 280                 285

Asn Ser Leu Leu His Glu Phe Val Glu Asp Trp Tyr Ser Gln Glu Phe
              290                 295                 300

Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                  325                 330                 335

Leu Thr Glu Thr Pro Ile Glu Tyr Leu Arg Trp Leu Asn Gln Gln Thr
              340                 345                 350

Arg Trp Ser Lys Ser Tyr Phe Arg Glu Trp Leu Tyr Asn Ala Met Trp
              355                 360                 365

Phe His Lys His His Leu Trp Met Thr Tyr Glu Ala Val Ile Thr Gly
              370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                  405                 410                 415

Gly Leu Ile Lys Ser Ser Phe Ala Ser Cys Leu Arg Gly Asn Ile Ile
              420                 425                 430

Met Val Phe Met Ser Leu Tyr Ser Val Leu Tyr Met Ser Ser Leu Leu
              435                 440                 445

Pro Ala Lys Met Phe Ala Ile Ala Thr Ile Asn Lys Ala Gly Trp Gly
              450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                  485                 490                 495

Tyr Lys Glu Ser Lys Lys Pro Phe Ser Glu Ser Lys Gln Thr Val Leu
              500                 505                 510

Ile Val Gly Thr Leu Leu Tyr Ala Cys Tyr Trp Val Met Leu Leu Thr
              515                 520                 525

Leu Tyr Val Val Leu Ile Asn Lys Cys Gly Arg Arg Lys Lys Gly Gln
530                 535                 540

Gln Tyr Asp Met Val Leu Asp Val
545                 550

<210> SEQ ID NO 2
<211> LENGTH: 1659
<212> TYPE: DNA
<213> ORGANISM: naked mole rat

<400> SEQUENCE: 2
atgcattgtg agaggtttct atgtatcctg agaataattg gaaccacgct ttttggagtc        60

```
tctcttctcc ttggaatcac agctgcttat atcgttggct accagtttat ccaaacggac      120
aattactatt tctcttttgg attatatggt gccttttag catcacatct catcatccaa       180
agcctatttg ccttttgga acacaggaaa atgaaaaaat ctctagaaac ccccattaag       240
ttgaacaaaa ctgttgctct ttgcatcgct gcatatcaag aagacccaga ctacttacga     300
aaatgtttgc aatctgtgaa aaggctcacc taccccggga ttaaggttgt catggtcata     360
gatgggaact cggatgatga cctgtacatg atggacatct tcagcgaagt catgggcagg     420
gacaagtcag ccacttacat ctggaaaaac aacttccacg aaaagggtcc tggtgagacg     480
gatgagtcac ataaagagag ctcacagcac gtgacacagt tggtcttgtc cagtaaaagt    540
gtgtgcatca tgcaaaagtg gggtggaaaa cgagaagtca tgtacacagc cttccgagcc    600
ctgggacgaa gtgtggatta tgtgcaggtt tgtgactccg ataccatgct ggaccctgcc    660
tcatctgtgg agatggtgaa agttttagaa gaagaccca tggttggagg agttgggggg     720
gatgtccaga ttttaaacaa gtatgattcc tggatctctt tcctcagcag tgtgagatac    780
tggatggctt ttaatataga aagggcctgt cagtcgtatt ttgggtgtgt ccagtgcatc    840
agtggacctc tggaatgta cagaaactcc ctgctgcatg agtttgtgga agactggtac     900
agtcaagaat tcatgggcaa ccagtgtagt tttggagatg acaggcacct aacaaatcgg     960
gtgctgagtc tgggctatgc cacaaaatac acagctcggt ccaagtgcct tactgaaaca    1020
ccaatcgaat atctcagatg gttgaaccag cagacccgtt ggagcaagtc ctacttccga    1080
gagtggctgt acaatgcaat gtggttccac aagcatcact tgtggatgac ctatgaagca    1140
gtcatcactg gatttttccc tttctttctc attgccacag taatccagct cttctacagg    1200
gggaaaattt ggaacatcct tctcttcttg ctaactgtcc agctggtagg gctcataaaa    1260
tcatcttttg ccagctgcct cagaggaaac atcatcatgg tctttatgtc tctctactca    1320
gtgttgtata tgtcaagttt acttcctgcc aaaatgtttg caatcgcaac aataaacaaa    1380
gctgggtggg gcacatccgg aaggaaaacc attgttgtca acttcatagg actcatccca    1440
gtgtcagttt ggtttacaat tctcctgggt ggtgtgattt tcaccattta taaggaatct    1500
aaaaagccat ttctgaatc caaacagaca gttttaattg ttggaacatt gctctatgca    1560
tgctattggg tcatgctgtt gacactgtac gtggttctca tcaataagtg tggcaggcgg    1620
aagaaaggac agcagtatga catggtgctg gacgtatga                           1659
```

<210> SEQ ID NO 3
<211> LENGTH: 165
<212> TYPE: PRT
<213> ORGANISM: naked mole rat

<400> SEQUENCE: 3

Pro Gly Glu Thr Asp Glu Ser His Lys Glu Ser Ser Gln His Val Thr
1               5                   10                  15

Gln Leu Val Leu Ser Ser Lys Val Cys Ile Met Gln Lys Trp Gly
            20                  25                  30

Gly Lys Arg Glu Val Met Tyr Thr Ala Phe Arg Ala Leu Gly Arg Ser
        35                  40                  45

Val Asp Tyr Val Gln Val Cys Asp Ser Asp Thr Met Leu Asp Pro Ala
    50                  55                  60

Ser Ser Val Glu Met Val Lys Val Leu Glu Glu Asp Pro Met Val Gly
65                  70                  75                  80

Gly Val Gly Gly Asp Val Gln Ile Leu Asn Lys Tyr Asp Ser Trp Ile

-continued

```
                    85                     90                      95

Ser Phe Leu Ser Ser Val Arg Tyr Trp Met Ala Phe Asn Ile Glu Arg
            100                 105                 110

Ala Cys Gln Ser Tyr Phe Gly Cys Val Gln Cys Ile Ser Gly Pro Leu
            115                 120                 125

Gly Met Tyr Arg Asn Ser Leu Leu His Glu Phe Val Glu Asp Trp Tyr
        130                 135                 140

Ser Gln Glu Phe Met Gly Asn Gln Cys Ser Phe Gly Asp Asp Arg His
145                 150                 155                 160

Leu Thr Asn Arg Val
                165
```